United States Patent
He et al.

(10) Patent No.: US 8,527,053 B2
(45) Date of Patent: *Sep. 3, 2013

(54) IMPLANTABLE STIMULATOR WITH INTEGRATED PLASTIC HOUSING/METAL CONTACTS AND MANUFACTURE AND USE

(75) Inventors: Tom Xiaohai He, Simi Valley, CA (US); Matthew Isaac Haller, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 676 days.

This patent is subject to a terminal disclaimer.

(21) Appl. No.: 12/822,061

(22) Filed: Jun. 23, 2010

(65) Prior Publication Data

US 2010/0262201 A1    Oct. 14, 2010

Related U.S. Application Data

(63) Continuation of application No. 11/238,240, filed on Sep. 29, 2005, now Pat. No. 7,761,165.

(51) Int. Cl.
 *A61N 1/00*     (2006.01)
(52) U.S. Cl.
 USPC .......................................................... 607/36
(58) Field of Classification Search
 USPC ........................................... 607/36–38
 See application file for complete search history.

(56) References Cited

U.S. PATENT DOCUMENTS

| | | | |
|---|---|---|---|
| 3,718,142 A | 2/1973 | Mulier | |
| 3,842,842 A | 10/1974 | Kenny et al. | |
| 5,193,539 A | 3/1993 | Schulman et al. | |
| 5,193,540 A | 3/1993 | Schulman et al. | |
| 5,312,439 A | 5/1994 | Loeb | |
| 5,522,861 A | 6/1996 | Sikorski et al. | |
| 6,051,017 A | 4/2000 | Loeb et al. | |
| 6,181,969 B1 | 1/2001 | Gord | |
| 6,505,072 B1 | 1/2003 | Linder et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,931,284 B2 | 8/2005 | Engmark et al. | |
| 7,194,309 B2 | 3/2007 | Ostroff et al. | |
| 7,263,401 B2 | 8/2007 | Scott et al. | |
| 7,330,756 B2 | 2/2008 | Marnfeldt | |
| 2004/0059392 A1 | 3/2004 | Parramon et al. | |
| 2006/0161215 A1 | 7/2006 | Naviaux | |

FOREIGN PATENT DOCUMENTS

| | | |
|---|---|---|
| WO | 9837926 | 9/1998 |
| WO | 9843700 | 10/1998 |
| WO | 9847301 | 10/1998 |

OTHER PUBLICATIONS

Non-Final Rejection mailed Dec. 4, 2008 for U.S. Appl. No. 11/238,240.
Final Rejection mailed May 7, 2009 for U.S. Appl. No. 11/238,240.
Non-Final Rejection mailed Oct. 9, 2009 for U.S. Appl. No. 11/238,240.

*Primary Examiner* — Scott Getzow
(74) *Attorney, Agent, or Firm* — Frommer Lawrence & Haug LLP; Bruce E. Black

(57) ABSTRACT

An implantable stimulator system includes a plastic housing, an electronic subassembly and at least one metal contact. The plastic housing defines an interior chamber and an exterior. The electronic subassembly is disposed in the interior chamber of the plastic housing. The at least one metal contact is integrally formed with the plastic housing, coupled to the electronic subassembly, and accessible from the exterior of the housing. The plastic housing and the at least one metal contact form a sealed structure around the electronic subassembly.

20 Claims, 5 Drawing Sheets

IMPLANTABLE STIMULATOR WITH INTEGRATED PLASTIC HOUSING/METAL CONTACTS AND MANUFACTURE AND USE

CROSS-REFERENCE TO RELATED APPLICATIONS

This patent application is a continuation of U.S. patent application Ser. No. 11/238,240, filed on Sep. 29, 2005, which is incorporated herein by reference.

FIELD

The invention is directed to implantable stimulators and stimulator components and methods of making and using the devices. The invention is also directed to implantable stimulators and stimulator components with integrated plastic housing and metal contacts, as well as methods of making and using the devices.

BACKGROUND

Implantable stimulators have been developed to provide therapy for a variety of disorders, as well as other treatments. For example, implantable stimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

As one example, spinal cord stimulation is a well accepted clinical method for reducing pain in certain populations of patients. Implantable stimulators have been developed to provide therapy for a variety of treatments. For example, implantable stimulators can be used to stimulate nerves, such as the spinal cord, muscles, or other tissue. An implantable stimulator can include an implanted control module (with a pulse generator), one or more leads, and an array of stimulator electrodes on each lead. The stimulator electrodes are implanted in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

BRIEF SUMMARY

One embodiment is an implantable stimulator system that includes a plastic housing, an electronic subassembly and at least one metal contact. The plastic housing defines an interior chamber and an exterior. The electronic subassembly is disposed in the interior chamber of the plastic housing. The at least one metal contact is integrally formed with the plastic housing, coupled to the electronic subassembly, and accessible from the exterior of the housing. The plastic housing and the at least one metal contact form a sealed structure around the electronic subassembly.

Another embodiment is a method of making an implantable stimulator system. In the method, a plastic housing is formed around at least one metal contact. The plastic housing defines an interior chamber and an exterior and the at least one metal contact is exposed in the interior chamber of the plastic housing, as well as at the exterior of the plastic housing. An electronic subassembly is disposed in the interior chamber of the plastic housing and coupled to the at least one metal contact. The interior chamber of the plastic housing is sealed.

Yet another embodiment is a method of stimulating tissue. In this method, an electrode array is implanted proximate to the tissue. A control module is also implanted. The control module includes a plastic housing defining an interior chamber and an exterior; an electronic subassembly disposed in the interior chamber of the plastic housing; and at least one metal contact integrally formed with the plastic housing, coupled to the electronic subassembly, and accessible from the exterior of the housing. The plastic housing and at least one metal contact form a sealed structure around the electronic subassembly. The electrode array is coupled to the control module using at least one lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to implantable stimulators and stimulator components and methods of making and using the devices. The invention is also directed to implantable stimulators and stimulator components with integrated plastic housing and metal contacts, as well as methods of making and using the devices.

Implantable stimulators include a housing that contains the electronic circuitry and power source that produce electrical pulses that are sent to the electrodes for stimulation of the neighboring tissue. It is preferable that the electronic circuitry and power source be held within the housing in a sealed environment for the protection of the user and the protection of the circuitry and power source. Once implanted, it is often preferable that the stimulator can be controlled and/or that the electrical source can be charged without removing the stimulator from the implanted environment.

Previously, implantable stimulators have been made using housings of metal (for example, titanium) and/or ceramic. Examples of such stimulators are found in U.S. Pat. Nos. 6,181,969; 6,516,227; 6,609,029; 6,609,032; and 6,741,892, all of which are incorporated by reference.

Figure 1:
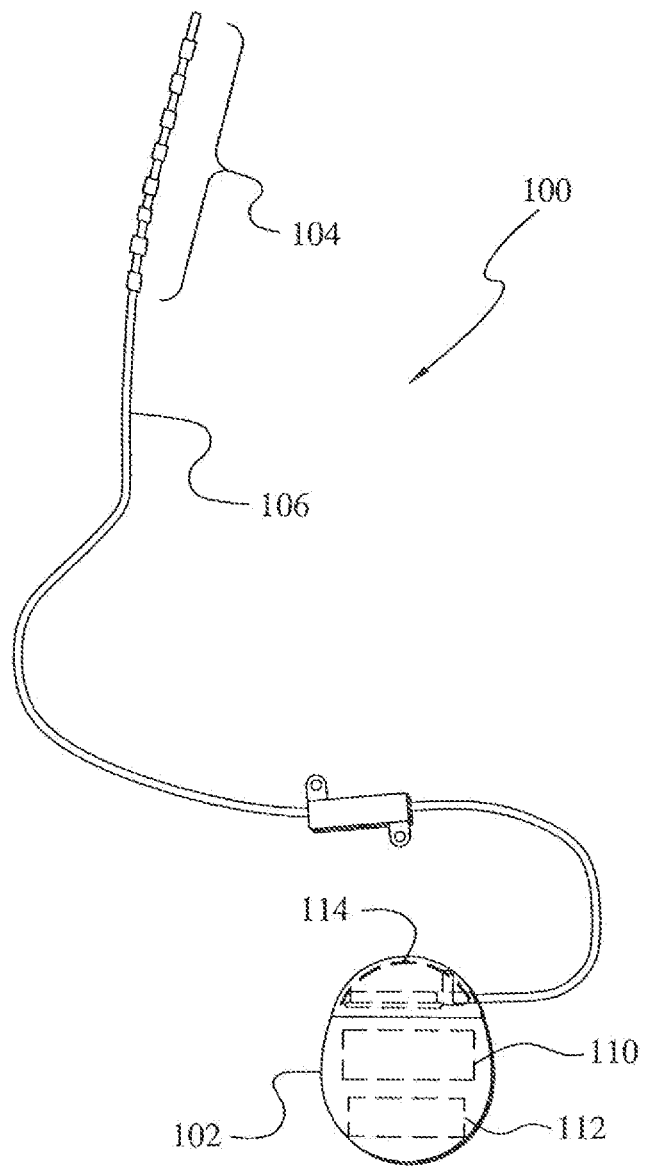
FIG. 1 is a schematic exterior perspective view of one embodiment of a stimulator system, according to the invention.

FIG. 1 illustrates schematically an implantable stimulator system 100, such as for stimulating a spinal cord stimulator. The implantable stimulator system includes a control module (e.g., a stimulator or pulse generator) 102, at least one electrode array 104, and at least one lead 106 coupling the control module to the electrode array(s). The control module 102 typically includes a housing 114 with an electronic subassembly 110 and, in at least some embodiments, a power source 112 disposed within a chamber in the housing. Preferably, the housing is resistant to moisture penetration into the chamber containing the electronic subassembly and power source. In some embodiments, water may diffuse through the housing. Preferably, the diffused water is relatively pure, without substantial ionic content, as deionized water is relatively non-conductive.

The housing 114 of the control module is formed of a plastic material with metal contacts integrated with the plastic material to connect lead contacts on the proximal part of the lead(s) 106 with the electronics subassembly 110 disposed in the housing 114. The plastic housing 114 can be formed of a plastic material that resists the transport of moisture into the interior of the housing and is sufficiently sturdy to protect the components on the interior of the housing from damage under expected implantation and usage conditions. Preferably, the material of the plastic housing is a hydrophobic polymer material. The plastic material of the housing can be a homopolymer, a copolymer formed using two or more different monomeric units, or a mixture of polymers or other materials. Examples of suitable polymer materials include polyolefins, polypropylene homopolymers and copolymers, teflon, and polyetheretherketone (PEEK). The plastic housing may also include additives such as, for example, fillers, plasticizers, antioxidants, colorants, and the like.

The thickness of the walls of the plastic housing may also impact the moisture permeability of the plastic housing. A minimum thickness needed to achieve a particular degree of resistance to moisture transport will often depend on the material selected for the housing, as well as any additives. In general, however, the thickness of the walls of the plastic housing is at least 600 µm and typically ranges from 600 to 1300 µm.

Optionally, the plastic housing can be covered, in full or in part, with a coating. The coating can be provided to improve or alter one or more properties of the plastic housing including, for example, biocompatibility, hydrophobicity, moisture permeability, leaching of material into or out of the plastic housing, and the like. The optional coating can be a polymer material, metallic material, or organic material. As an example, the plastic housing may be coated with an inorganic material, such as, for example, silicon dioxide, silicon nitride, titanium dioxide, or the like, to reduce moisture permeability. As another example, a silicone coating may be used to improve biocompatibility. In yet another example, a coating can be applied which contains a compound, such as, for example, a drug, prodrug, hormone, or other bioactive molecule, that can be released over time when the stimulator is implanted. (In another embodiment, the plastic housing itself may include such a compound to be released over time after implantation.) In some embodiments, the coating includes two or more layers of the same or different materials. For example, alternating layers of inorganic materials can be deposited as a coating to improve resistance to moisture transport through the plastic housing.

The formation of the coating can be accomplished using any method including, for example, dip-coating, sputtering, reactive sputtering, physical or chemical vapor deposition, spray coating, electroplating, electroless plating, and the like. The coating can be applied before the other stimulator components have been assembled with the plastic housing or at any other point in the stimulator manufacturing process including applying the coating after the stimulator has been completely assembled. Typically, the coating is non-conductive. A thin conductive coating may also be used to increase moisture resistance. Such thin coatings will generally not significantly affect the electromagnetic transparency of the housing due to the high resistance of the coating to the generation of eddy currents.

Figure 2:
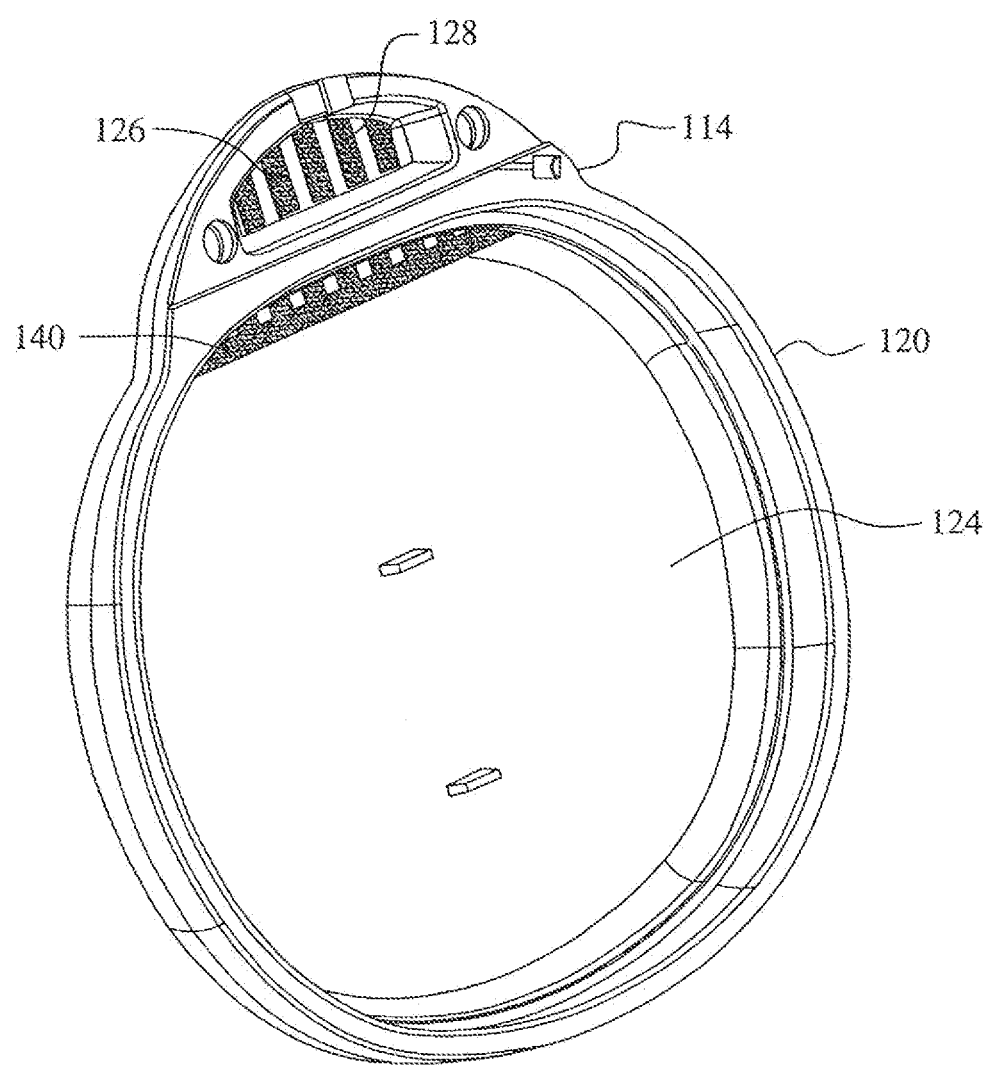
FIG. 2 is a perspective view of one embodiment of a component of a housing of the stimulator system of FIG. 1.
Figure 3:
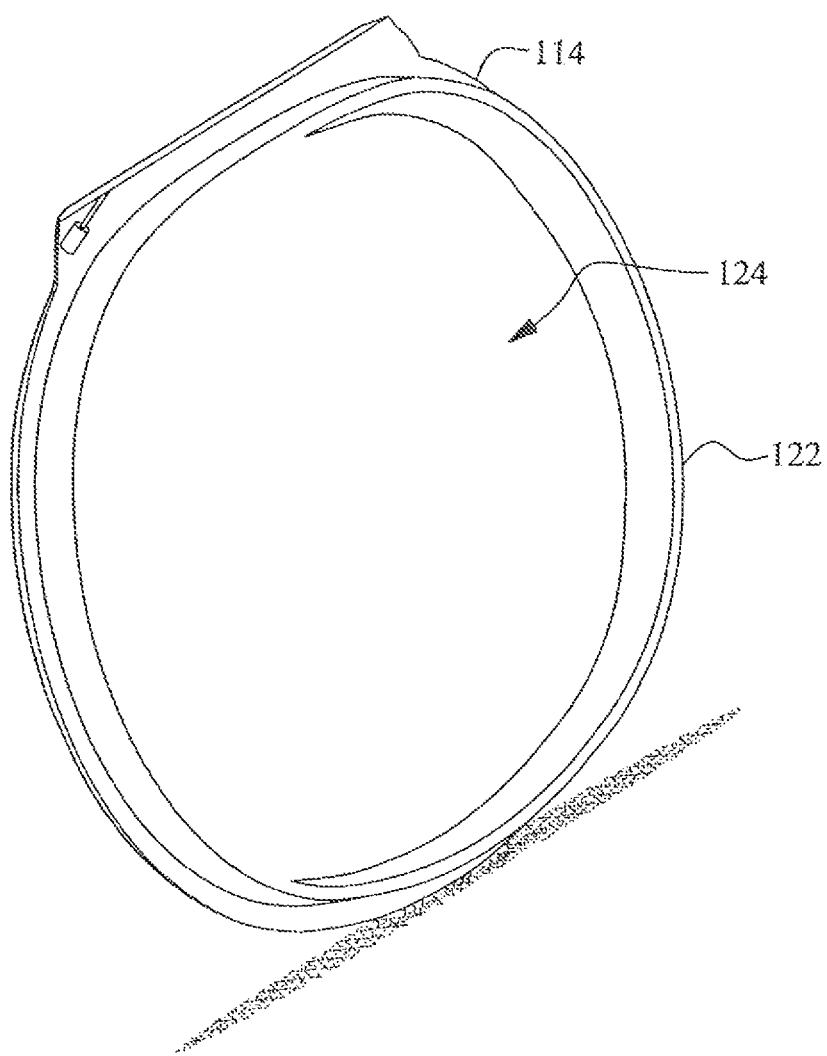
FIG. 3 is a perspective view of one embodiment of another component of a housing of the stimulator system of FIG. 1.

FIGS. 2 and 3 illustrated one embodiment of the housing where the plastic housing includes a first portion 120 (FIG. 2) and a second portion 122 (FIG. 3). The first and second portions 120, 122 can be formed separately and then brought together and sealed to produce the housing 114 (see FIG. 1). The portions together define a chamber 124 into which the electronics subassembly 110 and power source 112 can be placed and then sealed to prevent or resist moisture transmission into the chamber. Sealing of the chamber can be accomplished using any method that couples the first and second portions 120, 122 together. Such methods include, but are not limited to, adhesively coupling the portions together or welding (e.g., laser welding), or otherwise heating, the seam between the two portions to melt the two portions together. It will be understood that the housing illustrated in FIGS. 2 and 3 is only one example of a suitable housing. Other housings can be formed using only a single portion or using three or more portions.

In addition, in the illustrated embodiment, the first portion 120 defines a compartment 126 into which a proximal end of the lead 106 can be inserted. The proximal end of the lead 106 has exposed lead contacts that are connected through the lead to the electrodes 104. These lead contacts are arranged to make contact with metal contacts 128 disposed in the compartment 126 of the housing 114. The metal contacts 128 are integrally formed with the first portion 120 of the plastic housing 114. The metal contacts 128 extend from the compartment 126 through the material of the plastic housing and into the chamber 124 where the metal contacts can be coupled to the electronic subassembly 110. In another embodiment, one or more (or all) of the metal contacts are exposed on an exterior surface of the housing 114. Generally at least a portion of the metal contacts is embedded in the plastic of the housing. In some embodiments, the lead 106 and metal contacts 128 form a single, integral unit so that the proximal end of the lead 106 forms the metal contacts and is molded into the housing 114. In these embodiments, there is no need to make a separate connection between lead contacts and the metal contacts. The lead is connected directly to the electronic subassembly 110.

Preferably, when the proximal end of the lead 106 is inserted into the compartment 126, the lead 106 and housing 114 make contact and seal the entrance to the compartment to resist moisture penetration into the compartment. In some embodiments, the lead is removable. In other embodiments, the lead can be permanently coupled to the control module using, for example, adhesive or welding (e.g., laser welding) the lead to the housing.

The integrated plastic housing 114 and metal contacts 128 can be formed by any method. One example of a suitable method includes positioning a metal contact assembly, as described below, inside a mold and then injection molding the plastic housing 114 or a portion of the plastic housing 114 (e.g., first portion 120) around the metal contact assembly. Other molding methods can also be used. Integrating the plastic housing 114 and metal contacts 128 in this manner can enhance the resistance of the chamber 124 to moisture penetration because the material of the plastic housing is molded around the metal contacts rather than forming openings through the housing to insert the metal contacts.

Figure 4:
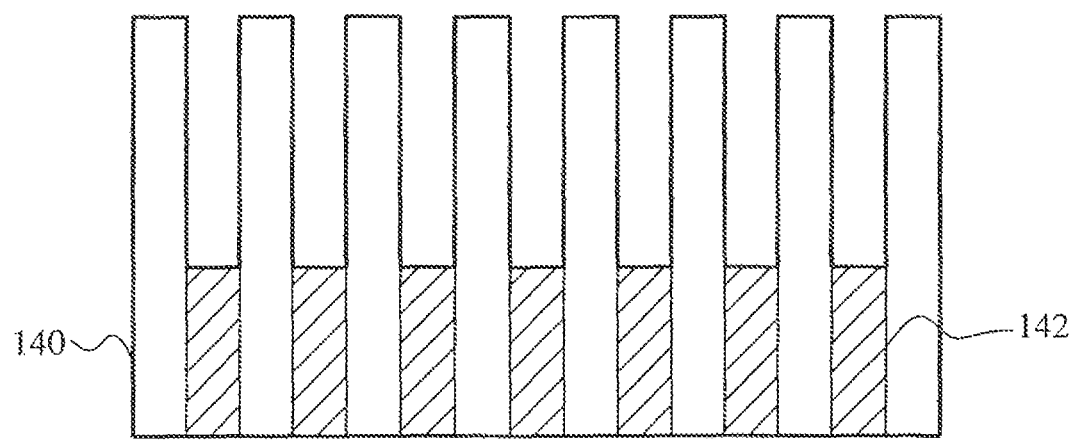
FIG. 4 is a view of one embodiment of a metal contact assembly, according to an embodiment of the invention.

The metal contact assembly can comprise separated individual contacts or a one or more integrated forms containing two or more individual contacts in each form or any combination of separated contacts and integrated forms. The individual contacts of an integrated form can be separated after the molding process. In one embodiment, a metal contact assembly 140, as illustrated in FIG. 4, is used for the molding process. This metal contact assembly 140 provides all of the metal contacts in a single structure where excess material 142 (indicated by shading in FIG. 4) can be removed (for example, by cutting, clipping, or otherwise eliminating this excess material) after the plastic housing or a portion of the plastic housing is formed around the metal contact assembly.

In another embodiment, the individual metal contacts 128 can be coupled together by one or more plastic pieces prior to insert molding the metal contacts into the housing 102. Preferably, the plastic piece(s) are made of the same material as the housing. These plastic pieces may be molded around the metal contacts and then this pre-molded plastic/metal arrangement can be insert molded into the housing.

The power source 112 is used for generating the stimulation current or may receive power from an external source. The power source can be any available power source including batteries, such as primary batteries or rechargeable batteries. Examples of other power sources include, but are not limited to, super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference. In one embodiment, a rechargeable power source, such a rechargeable battery or super capacitors, is used In other embodiments, power may be supplied from an external source. Preferably, the power source 112 is resistant to moisture that may diffuse through the Material of the plastic housing 114.

The control module 102 is optionally programmable to allowing programming of one or more functions such as, for example, the selection of electrodes for delivering stimulation, the selection of electrodes as anode or cathode, the amplitude of the stimulation current, the duration of the stimulation current, and the periodicity of the stimulation current. In some embodiments, the control module 102 can be accessed using a programming unit external to the body of the patient to alter or modify these functions.

The electrode array 104 typically includes two or more electrodes. In some embodiments, the electrode array includes four, six, eight, 10, 16, or more electrodes. The electrodes can be in a linear array, for example, disposed along an electrode lead, or in a two-dimensional array, for example, forming two or more columns or rows, or any other arrangement. Non-limiting examples of suitable electrode arrays are illustrated in U.S. Pat. No. 6,516,227, incorporated herein by reference. In some embodiments, the electrode array is disposed on the distal end(s) of one or more leads.

The lead 106 includes a set of conductors (for example, one conductor per electrode of the electrode array) within a non-conductive sheathing. Each conductor couples one or more electrodes to each metal contact 128 of the control module. Non-limiting examples of suitable control modules, electrode arrays, and leads that can be used or modified for use in the present stimulator system are illustrated in U.S. Pat. Nos. 6,181,969; 6,516,227; 6,609,029; 6,609,032; and 6,741,892, all of which are incorporated by reference.

The electrodes of the electrode array 104 form the anode(s) and cathode(s) of the lead 106. These electrodes can be formed of the same or different conductive materials. Preferably, the electrodes are formed of materials that do not substantially corrode under the operating conditions and in the operating environment for the expected lifetime of the stimulator. Examples of suitable materials include metals, alloys and other conductive materials such as, for example, titanium, iridium, platinum, platinum iridium, and the like.

Figure 5:
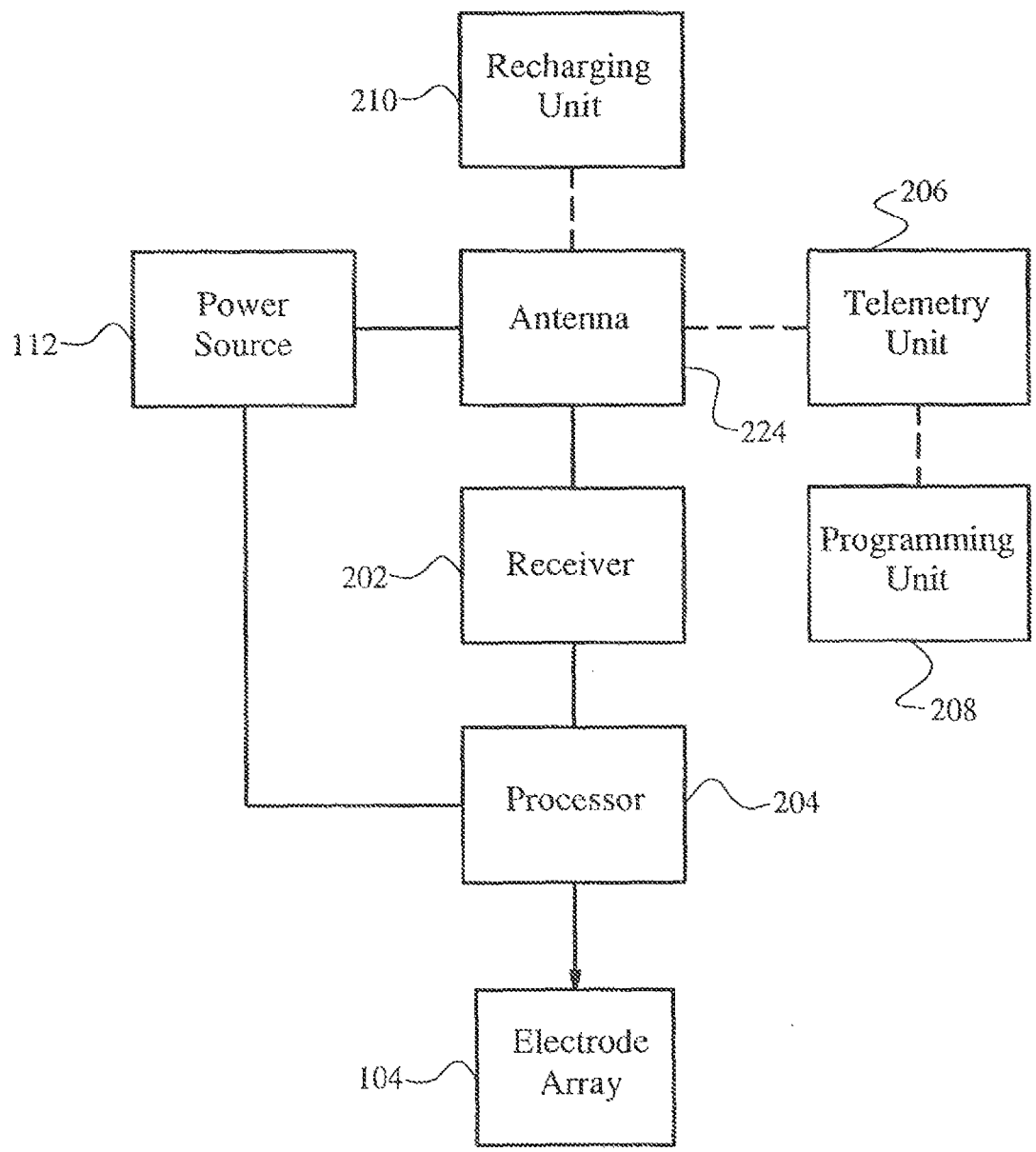
FIG. 5 is a schematic overview of components for a system for stimulating body tissues.

The electronic subassembly 110 is disposed in the housing 114 of the control module 102 and provides the electronics used to operate the stimulator and generate the electrical pulses at the electrodes of the electrode array 104 to produce stimulation of the body tissues. The electronic subassembly 110 is coupled to the electrode array(s) 104 via the metal contacts 128 and lead(s) 106. FIG. 5 illustrates one embodiment of components of the electronic subassembly and associated units. It will be understood that the electronic subassembly can include more, fewer, or different components and can have a variety of different configurations including those configurations disclosed in the stimulator references cited above. Some or all of the components of the electronic subassembly can be positioned on one or more circuit boards or similar carriers within the plastic housing, if desired.

In the illustrated embodiment, a processor 204 is provided to control the timing and electrical characteristics of the stimulator. For example, the processor can, if desired, control one or more of the timing, periodicity, strength, duration, and waveform of the pulses. Any processor can be used and can be as simple as an electronic device that produces pulses at a regular interval or the processor can be capable of receiving and interpreting instructions from an external programming unit 208 that allows modification of pulse characteristics. In the illustrated embodiment, the processor 204 is coupled to a receiver 202 which, in turn, is coupled to the optional antenna 224. This allows the processor to receive instructions from an external source to direct the pulse characteristics. The optional antenna, or another antenna, can be used to recharge a rechargeable power source or provide power to the stimulator.

In one embodiment, the antenna 224 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the implanted stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 224 and receiver 202 can be used to modify or otherwise direct the operation of the stimulator. For example, the signals may be used to modify the pulses of the stimulator such as modifying one or more of pulse duration, pulse frequency, pulse waveform, and pulse strength. The signals may also direct the stimulator to cease operation or to start operation or to start charging the battery. One advantage of a plastic housing is that plastic is typically more transparent to RF signals than metallic or ceramic materials. Thus, in some instances RF signals may be more reliably received or transmitted and received with less power loss when a plastic housing is used. Use of a metal housing, e.g., a titanium housing, with a rechargeable battery can be problematic because the housing can generate eddy currents during inductive recharging. As a result the rate of recharging is limited as well as the efficiency of power transfer. Use of a plastic housing eliminates or reduces generation of heat, and can improve the efficiency of transfer of energy into the rechargeable battery, since no eddy currents result.

Optionally, the stimulator may include a transmitter (not shown) coupled to the processor and antenna for transmitting signals back to the telemetry unit 206 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 224 can have any form. In one embodiment, the antenna comprises a coiled wire that is wrapped at least partially around the electronic subassembly within the plastic housing.

In one embodiment, a rechargeable battery may be used as the power source 112 and therefore the power source should be recharged occasionally. For example, the rechargeable power source may be a rechargeable battery. An external recharging unit 210 may be used to inductively couple the antenna 24 that may be coupled to the receiver 202.

The stimulator can be implanted into the body tissue using a variety of methods including surgical methods.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable control module configured and arranged for coupling to a lead and electrode array, comprising:
    a plastic housing defining an interior chamber and an exterior;
    an electronic subassembly disposed in the interior chamber of the plastic housing; and
    a plurality of metal contacts integrally formed with the plastic housing, coupled to the electronic subassembly, and accessible from the exterior of the housing,
    wherein the housing is formed around the plurality of metal contact such that the plastic housing and the plurality of metal contacts form a sealed structure around the electronic subassembly.

2. The implantable control module of claim 1, wherein the plastic housing defines a compartment that is accessible from the exterior of the plastic housing through an opening.

3. The implantable control module of claim 2, wherein the plurality of metal contacts extend from the compartment into the interior chamber, and wherein a portion of the plurality of metal contacts disposed in the compartment are directly coupleable to the lead.

4. The implantable control module of claim 1, wherein the plastic housing comprises polyetheretherketone.

5. The implantable control module of claim 1, wherein the plastic housing comprises walls having a thickness in a range of 600 to 1300 μm.

6. The implantable control module of claim 1, wherein the plastic housing comprises a hydrophobic polymer material.

7. The implantable control module of claim 1, further comprising a coating disposed on at least a portion of the housing.

8. The implantable control module of claim 7, wherein the coating comprises silicon dioxide, silicon nitride, or titanium dioxide.

9. The implantable control module of claim 7, wherein the coating comprises silicone.

10. The implantable control module of claim 7, wherein the coating comprises a drug, prodrug, or hormone configured and arranged for release over time when the control module is implanted.

11. The implantable control module of claim 1, wherein the plurality of metal contacts are integrally formed with the housing by injection molding at least a portion of the plastic housing around a metal contact assembly comprising the plurality of metal contacts.

12. A method of making an implantable control module, the method comprising:
    molding a plastic housing of the control module around a plurality of metal contacts, wherein the plastic housing defines an interior chamber and an exterior and the plurality of metal contacts are exposed in the interior chamber of the plastic housing and are exposed at the exterior of the plastic housing;
    disposing an electronic subassembly in the interior chamber of the plastic housing;
    coupling the electronic subassembly to the plurality of metal contacts; and
    sealing the interior chamber of the plastic housing,
    wherein the housing is molded around the plurality of metal contacts such that the plastic housing and the plurality of metal contacts form a sealed structure around the electronic subassembly.

13. The method of claim 12, wherein forming a plastic housing comprises injection molding a plastic housing around a metal contact assembly and forming the plurality of metal contacts from the metal contact assembly.

14. The method of claim 13, wherein forming the plurality of metal contacts comprises removing material from the metal contact assembly to form a plurality of metal contacts.

15. The method of claim 13, wherein forming a plastic housing comprises forming at least two housing portions and wherein sealing the interior chamber of the plastic housing comprises sealing the at least two housing portions together.

16. The method of claim 15, wherein forming at least two housing portions comprises forming one of the housing portions around the metal contact assembly.

17. The method of claim 12, further comprising disposing a coating over at least a portion of the housing.

18. The method of claim 17, wherein the coating comprises silicon dioxide, silicon nitride, titanium dioxide, or silicone.

19. The method of claim 17, wherein the coating comprises a drug, prodrug, or hormone configured and arranged for release over time when the control module is implanted.

20. The method of claim 17, wherein disposing a coating comprises forming multiple coating layers on the housing.

* * * * *